5/12/81 XR 4,266,548

United States Patent [19]
Davi

[11] 4,266,548
[45] May 12, 1981

[54] APPARATUS FOR AND METHOD OF UTILIZING ENERGY TO EXCISE PATHOLOGICAL TISSUE

[76] Inventor: S. K. Davi, 4620 N. Park Ave., Apt. 1408 West, Chevy Chase, Md. 20015

[21] Appl. No.: 970,132

[22] Filed: Dec. 18, 1978

[51] Int. Cl.³ .................... A61B 17/00; A61N 5/01
[52] U.S. Cl. .................... 128/303.1; 350/358; 219/121 LM; 219/121 LR; 219/121 LW; 331/94.5 K
[58] Field of Search .................... 128/303.1, 395–398; 219/121 L, 121 LM, 121 LG, 121 LU, 121 LN, 121 LW, 121 LM, 121 LR; 331/94.5 K; 350/358

[56] References Cited

U.S. PATENT DOCUMENTS

| | | | |
|---|---|---|---|
| Re. 29,557 | 2/1978 | Isaacs et al. | 350/358 |
| 3,203,176 | 11/1965 | Vassiliadis et al. | 128/303.1 |
| 3,383,491 | 5/1968 | Muncheryan | 219/121 L |
| 3,422,246 | 1/1969 | Wetzel | 219/121 L |
| 3,456,641 | 7/1969 | Yokota et al. | 128/4 |
| 3,467,098 | 9/1969 | Ayres | 128/303.1 |
| 3,471,215 | 10/1969 | Snitzer | |
| 3,494,354 | 2/1970 | Yokota et al. | 128/6 |
| 3,576,965 | 5/1971 | Gugger | 219/121 L |
| 3,632,205 | 1/1972 | Marcey | 355/53 |
| 3,653,384 | 4/1972 | Swope | 128/303.1 |
| 3,659,613 | 5/1972 | Bredmeir | 128/395 |
| 3,661,441 | 5/1972 | Uchida | 350/358 |
| 3,710,798 | 8/1973 | Bredemeir | 128/303.1 |
| 3,749,878 | 7/1973 | Sullivan | 219/121 L |
| 3,769,963 | 11/1973 | Goldman et al. | 128/303.1 |
| 3,804,095 | 4/1974 | Bredemeier | 128/303.1 |
| 3,858,577 | 1/1975 | Bass et al. | 128/8 |
| 3,865,114 | 2/1975 | Sharon | 128/303.1 |
| 3,906,953 | 9/1975 | Wallace et al. | 128/303.1 |
| 3,920,980 | 11/1975 | Nath | 219/121 L |
| 3,930,504 | 1/1976 | deLaforcade | 128/303.1 |
| 3,982,541 | 9/1976 | L'Esperance, Jr. | 128/303.1 |
| 4,069,823 | 1/1978 | Isakov et al. | 128/303.1 |
| 4,108,174 | 8/1978 | Slivenko | 128/214 R |
| 4,122,853 | 10/1978 | Smith | 128/303.1 |
| 4,141,362 | 2/1979 | Wurster | 128/303.1 |
| 4,169,976 | 10/1979 | Cirri | 219/121 LN |

FOREIGN PATENT DOCUMENTS

| | | | |
|---|---|---|---|
| 1058694 | 6/1959 | Fed. Rep. of Germany | 128/4 |
| 2424726 | 4/1975 | Fed. Rep. of Germany | 128/303.1 |
| 2511131 | 9/1976 | Fed. Rep. of Germany | 128/303.1 |
| 2620846 | 11/1977 | Fed. Rep. of Germany | 128/303.1 |
| 2385372 | 10/1978 | France | 128/303.17 |

OTHER PUBLICATIONS

Kulcke et al., IBM Journal of R & D, vol. 8, Jan. 1964 pp. 64–67–TK 7885 A1I15.
Aas., H. G. et al., Journal of Acoustical Society of America; vol. 36, #10 10/64 pp. 1906-1913-Application of Ultrasonic Standing Waves . . . Beam Scanning.

*Primary Examiner*—Robert W. Michell
*Assistant Examiner*—Arthur S. Rose
*Attorney, Agent, or Firm*—Lowe, King, Price and Becker

[57] ABSTRACT

Pathological tissue is excised with a beam from a laser that is coupled through a flexible, optical wave guide to a collimator that reduces the beam cross sectional area by variable, controlled amounts. A transparent bore or a graphite cannula couples the beam exiting the collimator to the tissue to vaporize same. An electrically responsive deflector gyrates the reduced cross sectional area beam about a bore sight axis aligned with the cannula bore so that the excised tissue has a frusto-conical volume. To excise different, displaced tissue regions, a position servo system moves the cannula so the bore sight axis moves in a plane at right angles to a plane on the exterior surface containing the pathological tissue.

20 Claims, 16 Drawing Figures

APPARATUS FOR AND METHOD OF UTILIZING ENERGY TO EXCISE PATHOLOGICAL TISSUE

FIELD OF THE INVENTION

The present invention relates generally to a method of and apparatus for excising pathological tissue from living animal and, more particularly, to such an apparatus and method wherein high intensity coherent, optical radiation is coupled to the tissue through a cannula.

BACKGROUND OF THE INVENTION

Lasers have been extensively utilized for excising pathological, exterior tissues, such as skin, and have been suggested for excising interior pathological tissues, by utilizing invasive techniques. The pathological tissue is excised in response to the laser producing high intensity electromagnetic fields that vaporize and damage the tissue lattice. The laser damage field coincides with the electromagnetic, optical field so that the size or volume of excised tissue can be very accurately controlled. The laser beam creates holes or cuts in the tissue by disrupting bonds in the chemical network of tissue. The problems involved in invasive, rather than noninvasive, laser surgery are well known and have been dealt with, to a certain extent, by others. For example, invasive laser systems, or laser systems which appear to be adaptable to invasive applications, are disclosed in the following United States Patents:

| | |
|---|---|
| Snitzer | 3,471,215 |
| Bredemeir | 3,659,613 |
| Ayres | 3,467,098 |
| Bredemeir | 3,710,798 |
| Bredemeir | 3,804,095 |
| Sharan | 3,865,114 |
| Wallace et al. | 3,906,953 |

A particular problem involved in invasive laser surgery is propagating the beam to the pathological tissue to be excised without damaging intermediate tissue between the pathological tissue and an opening in the body cavity through which the beam must enter. High intensity, coherent, optical radiation derived from the laser has a tendency to heat guiding structures through which it propagates. If the guiding structure contacts the intermediate tissue, there is a tendency for the intermediate tissue to be excessively heated and possibly burned to a serious extent. An instrument that contacts the intermediate tissue must be chemically inert with the tissue so that it does not cause any infection, thermal burns or other deleterious effects on that tissue. In addition, it is desirable for the cross sectional, circular area of the irradiating beam to be small in certain instances and larger in other instances. It is also frequently desirable to excise the pathological tissue so that the cross section of the excised tissue, in a plane at right angles to the exterior surface of the tissue, is frusto-conical, with the largest face of the frusto-conical section being below the surface to reduce blood flow from the tissue and promote faster healing of the treated area of the organ.

It is accordingly, an object of the present invention to provide a new and improved apparatus for and method of excising pathological tissue with a laser beam.

A further object of the invention is to provide a new and improved instrument for and method of excising pathological tissue from the interior of a living animal with a laser beam that is introduced into the body cavity without causing any substantial adverse effects on tissue within the body cavity between the entrance to the body cavity and the pathological tissue.

A further object of the invention is to provide a laser instrument for and method of excising pathological tissue wherein laser energy is coupled to the pathological tissue without substantially heating intermediate tissue between an opening in the body cavity and the site of the pathological tissue.

An additional object of the invention is to provide a laser instrument for excising pathological tissue within the body cavity wherein energy from the laser source irradiates the pathological tissue with an optical wave guiding cannula that is chemically inert with intermediate tissue between the opening to the body cavity and the pathological tissue.

Still another object of the invention is to provide a new and improved apparatus for and method of excising pathological tissue from the interior of a living organism by forming relatively small diameter, substantially frusto-conical cross sectioned excised regions in the tissue, wherein the conical cross section increases as a function of depth from the surface to the tissue.

BRIEF DESCRIPTION OF THE INVENTION

In accordance with one aspect of the invention, a laser beam is invasively coupled to pathological tissue via an optically transparent interior portion of a pyrolytic graphite cannula that is inserted through an opening in a body cavity into proximity with the tissue. The pyrolytic graphite cannula has a crystalline axis disposed so that there is minimum heat transfer from the interior, optically transparent portion thereof to the exterior wall thereof. Thereby, any heat radiated to the cannula internal wall by the laser beam is substantially decoupled from healthy tissue through which the cannula is inserted, and the healthy tissue is not overheated and damaged in response to heat radiating from the laser propagating through the cannula. In addition, the pyrolytic graphite is chemically inert with tissue in contact with it, whereby the intermediate tissue does not become infected through the use of the cannula.

The cross sectional area of the cannula transparent portion determines, to a large extent, the cross sectional area of the laser beam irradiating the pathological tissue. To control the resolution of the excised tissue, cannulas having different transparent cross sectional areas and outside diameters are employed by being inserted into a holding chuck that is maintained outside of the body cavity.

For certain beam diameters, the cannula interior transparent region is formed as an air filled bore extending along the longitudinal axis of the cannula. The wall of the bore is plated with a relatively thin metal, preferably gold, optically reflective film that is covered by a protective, dielectric film. The gold film reflects any stray, disbursive laser beam energy that impinges on the internal wall of the bore, to minimize heating of the interior diameter of the cannula and to increase the energy of the beam exiting the cannula and irradiating the pathological tissue. For other applications, where the transparent cross section of the cannula is very small, in situations where it would be difficult to coat the inner diameter of the cannula with a metal, the entire bore is filled with a polycrystalline dielectric that is transparent to the laser energy.

The laser beam coupled to the input of the cannula, outside of the body cavity, is derived from a collimator that reduces the beam diameter relative to the diameter of the beam coupled to an input aperture of the collimator from a flexible, optical, wave guide that is responsive to the laser source. The collimator is adjustable to vary the cross sectional area of the beam exiting it and coupled to the inlet of the cannula. By varying the diameter of the beam exiting the collimator and coupled to the cannula, the resolution of the beam irradiating the pathological tissue is controlled. The energy density in the beam is also controlled by the collimator assist in determining the depth of excised tissue.

In accordance with another aspect of the invention, the excised tissue has a substantially frusto-conical volume having its smaller base on the initially irradiated, exterior surface of the organ being irradiated. The larger base within the organ has a concave configuration. The frusto-conical volume is desirable in many instances because the pathological tissue is usually in the interior of the organ, rather than on its surface, whereby a minimum amount of healthy tissue is removed.

The frusto-conical excision is provided by deflecting the beam coupled to the entrance aperture of the cannula an electrically responsive optical deflecting crystal. The crystal selectively deflects the beam relative to the cannula bore sight axis, so that for each position of the cannula the beam is gyrated about the cannula bore sight axis. The beam is preferably pulsed by employing either a pulsed laser source or a continuous wave laser source that is mechanically coupled to the cannula by a shutter in the collimator. For each laser energy pulse passing through the cannula at a fixed cannula position, a different beam deflection angle is provided by the electrically responsive optical deflector, whereby a series of beam pulses irradiate differing, but overlapping areas of pathological tissues to be excised. The beam deflector can either be electro-optic or acousto-optic, depending upon the wavelength of the laser beam; both types of deflectors are preferably driven in a step-wise manner.

To position the cannula so that differing regions of the pathological tissue can be excised, the cannula is mounted so that its bore sight axis is coincident with an axis extending at substantially right angles through an exterior surface of the tissue, the cannula is driven so its bore sight axis moves in a plane substantially at right angles to a plane on the exterior surface of the organ containing the tissue. Preferably, the cannula is moved so its bore sight axis moves in a plane at right angles to the exterior surface of the tissue in response to a position servo feedback control system responsive to input position control signals and an encoded signal indicative of the cannula position relative to its mounting. The cannula is also moved on its mounting so that it is translated along its bore sight axis. Thereby, different discrete and separate tissue layers can be excised by inserting the cannula to different positions within the body cavity. For example, if it is desired to remove pathological tissue from a portion of an organ, such as the heart, the cannula can first be inserted into the body cavity and the laser activated to pierce the pericardial sac. Then the cannula is inserted through the hole in the sac into proximity with a wall of the heart and the laser is reactivated to remove pathological tissue from the wall of chambers of the heart. In such an instance, it would also be frequently desirable to change the cannula to provide increased resolution for excising tissue within the wall of the chambers of the heart, relative to tissue in the pericardial sac. For heart muscle repair (as is appropriate in the treatment of rhythm disturbances and conduction abnormalities), the instrument would be utilized with a heart monitoring apparatus, such as an EKG and an array of electrodes placed on the epicardial surface of the heart, to determine if the pathological tissue removal resulted in the restoration of normal function.

One particular application of the instrument is for the treatment of cardiac myopathies due to structural and functional abnormalities. Some examples of cardiac myopathies are (1) the Wolff-Parkinson-White syndrome (WPW syndrome), (2) supra-ventricular, (3) ventricular tachycardias, (4) nodal tachycardias due to failure of pacemakers below the AV node, (5) firing of an ectopic foci due to myocardial change such as atrial flutter or fibrillation and other reentry mechanisms and/or circus pathways (where two areas of the heart are inhomogeneous).

The Wolff-Parkinson-White syndrome is a classic reentrant mechanism and is characterized by the following electrocardiographic features: (1) abnormally short P-R intervals, (2) distortion of QRS complex, resulting from the appearance of a delta wave due to accessory pathways of conduction from the atrium to the ventricle (due to the presence of anamolous Kent bundles. The interruption of the anamolous Kent bundles is a treatment for WPW syndrome. The location of Kent bundles is done by epicardial mapping in combination with lasing and excision procedures in accordance with an aspect of the invention. The invention can also be utilized in connection with neural disorders, with the assistance of electro-cortical mapping. Other applications of the apparatus include selective excision of tissue from bone marrow and other internal organs. Hence, the invention has particular utility in connection with surgical procedures that involve excision of pathological tissues in areas that are not easily accessible. These procedures are performed without extensive dissection and/or trauma to normal tissues in the cannula path leading to the pathological lesion. In contrast, prior techniques for excising pathological tissue from the heart have involved opening the pericardial sac by mechanically cutting a relatively lengthy slit in the sac and then removing the pathological tissue by mechanical cutting surgical instruments such as a scalpel. With the present surgical invention, it is merely necessary to make a relatively small diameter circular hole in the sac and a smaller diameter circular cavity in the heart or other organs in question.

It is, accordingly, a further object of the invention to provide a new and improved method of and apparatus for excising pathological tissues at areas that are not readily accessible in a body cavity, without extensive dissection and trauma.

A further object of the invention is to provide a new and improved method of excising pathological tissue from the heart without mechanically opening the pericardial sac.

The above and still further objects, features and advantages of the present invention will become apparent upon consideration of the following detailed description of several specific embodiments thereof, especially when taken in conjunction with the accompanying drawings.

DETAILED DESCRIPTION OF THE DRAWINGS

Figures 1, 2:
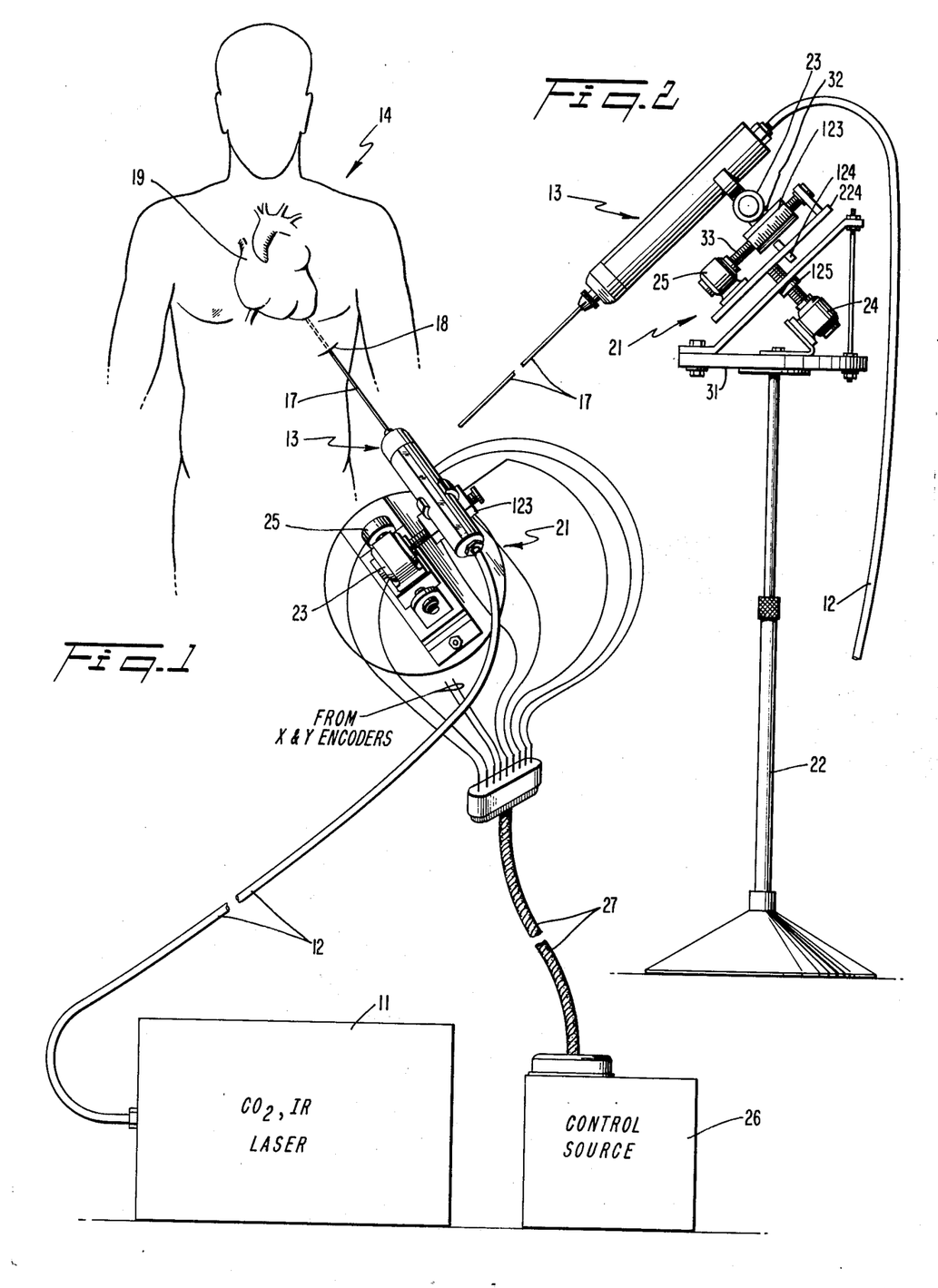
FIG. 1 is an overall perspective view of an instrument in accordance with the invention.
FIG. 2 is an elevation view of a portion of the instrument illustrated in FIG. 1.

Reference is made to FIGS. 1 and 2 of the drawings wherein a relatively high powered (two to four watts) source 11, such as a carbon dioxide laser with wavelength 10.6μ or a neodymium, semiconductor laser emits a circular cross sectional beam of monochromatic coherent optical radiation, in the infrared region. The beam derived from laser source 11 can be either a continuous wave beam or a pulsed beam. If the beam is continuous wave, it is normally blocked by a shutter, as described infra. Because pulsed lasers are not as monochromatic and do not have a pure Gaussian beam distribution and are not easily controlled in energy distribution as continuous wave lasers, the latter are preferred. The coherent beam derived from laser source 11 is coupled by flexible, optical wave guide 12 to an input aperture of collimator 13 that reduces the diameter of the beam propagating from the exit aperture of wave guide 12. Collimator 13 can be adjusted to reduce the diameter of the beam coupled from its entrance to its exit aperture by differing amounts, depending upon the desired resolution and energy density of the laser beam invasively coupled to pathological tissue in patient 14. The beam propagating from the exit aperture of collimator 13 is selectively deflected by crystal 15, FIG. 4, and thence focused by lens 9 and coupled through optically transparent bore or central region 16 of graphite cannula 17 which extends through aperture 18 in the body cavity, in proximity to an organ being treated, such as a heart 19. The focusing lens 9 is a multi-element lens with a depth of field of approximately 0.33 inches and a focal length of approximately 5 inches so its image is focused on the pathological tissue lens 9 and is placed less than half a millimeter from the entrance aperture bore of cannula 17.

Adjustable collimator 13, deflecting crystal 15 and beam guiding cannula 17, together form an optical control mechanism 21. Optical control mechanism 21 is mounted on stand 22 to enable the bore sight axis of cannula 17 to be moved in a plane parallel to the surface of the treated organism defined as the X-Y plane, in response to control signals respectively supplied to X and Y servo motors 23 and 24. Cannula 17 is moved at right angles to the surface of treated organism 19 along the cannula bore sight axis (the Z direction), in response to a control signal applied to Z axis motor 25. The control signals for motors 23-25 are derived from control source 26 and supplied to the motors 23-25 via a flexible electric cable 27. Cable 27 also includes leads for supplying a pair of X and Y deflection signals to crystal 15, as well as leads to control actuator 28 that opens normally closed shutter 29 in collimator 13.

Motor 24 is fixedly mounted relative to stand 22 by having its winding and housing fixedly mounted on platform 31, which is, in turn, fixedly mounted on stand 22. The shaft of motor 24 drives table 224 on which is fixedly mounted the winding and housing of Y motor 25. On table 32 are fixedly mounted the winding and housing of Z motor 23 to which assembly 21 is connected by a suitable rack and gearing mechanism 33. Motors 23, 24 and 25 are at mutually right angles to each other to provide for the Z, Y and X movements of assembly 21. The relative positions of table 224 in the X, Y and Z directions are determined by position transducers or encoders 123, 124 and 125 that feed X, Y and Z signals back to control source 26, which drives motors 23-25 until the position of cannula corresponds with the programmed control signals for the cannula position.

Preferably, flexible optical wave guide 12 is fabricated from alumina, because alumina is stable for the high operating temperatures (1700° to 1800° C.) that occur in response to the 2-4 watt energy emitted by laser 11. In addition, wave guide 12 has a suitable coefficient ($5.5 \times 10^{-6}$ per °C.) of thermal linear expansion (hence high thermal shock resistance), so that it remains stable and does not perturbate the $TEM_{02}$ mode energy derived from source 11. The alumina optical wave guide 12 is also desirable because it has a low thermal conductivity of approximately 0.007 to 0.05 cal $(S.cm.C°)^{-1}$.

Figures 3, 4, 5:
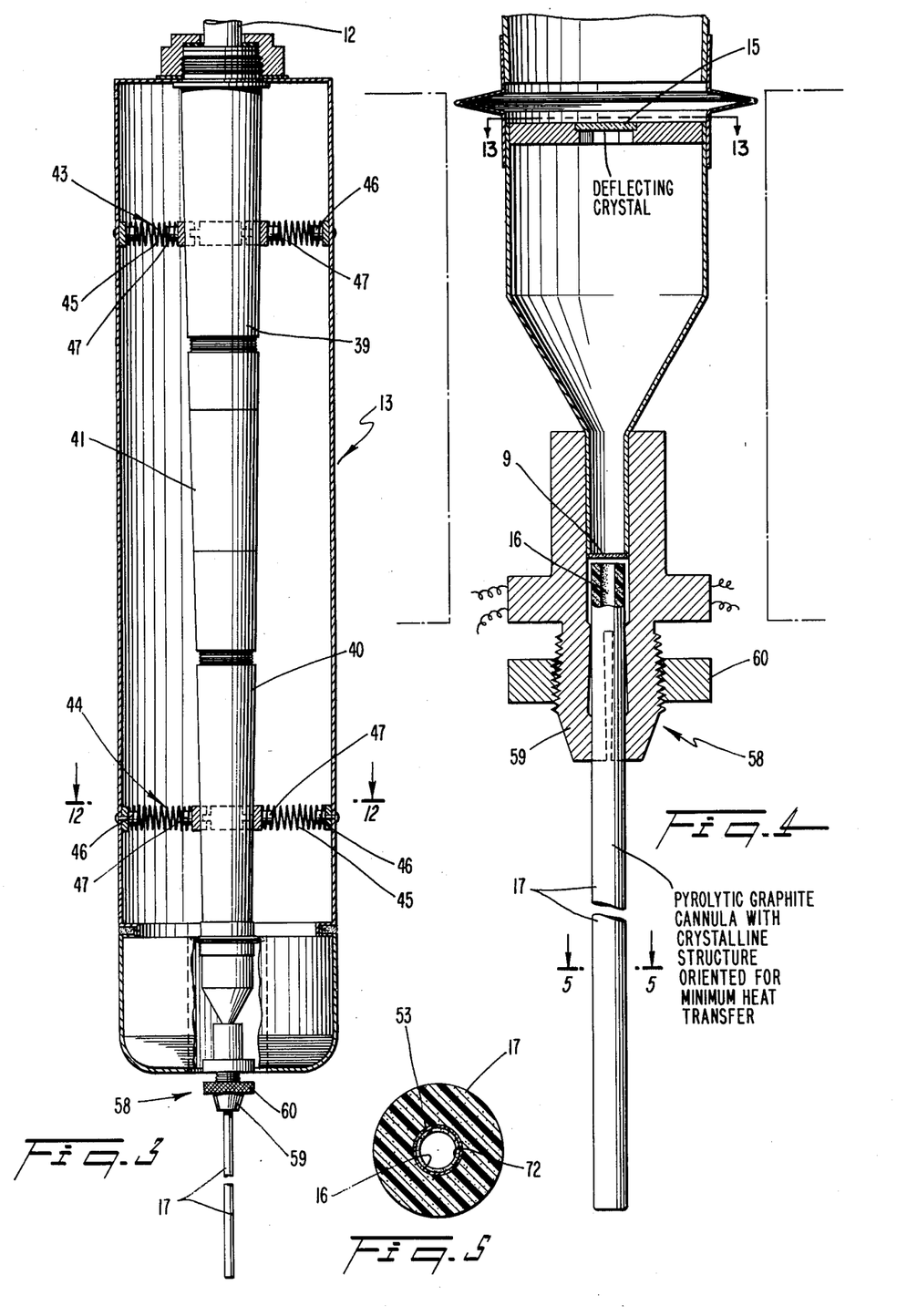
FIG. 3 is a side view of a collimator and cannula in accordance with the present invention.
FIG. 4 is an enlarged view of the cannula and the proximate end of the collimator illustrated in FIG. 3.
FIG. 5 is a side sectional view of the cannula, taken through lines 5—5, FIG. 4.
Figures 11, 12, 13:
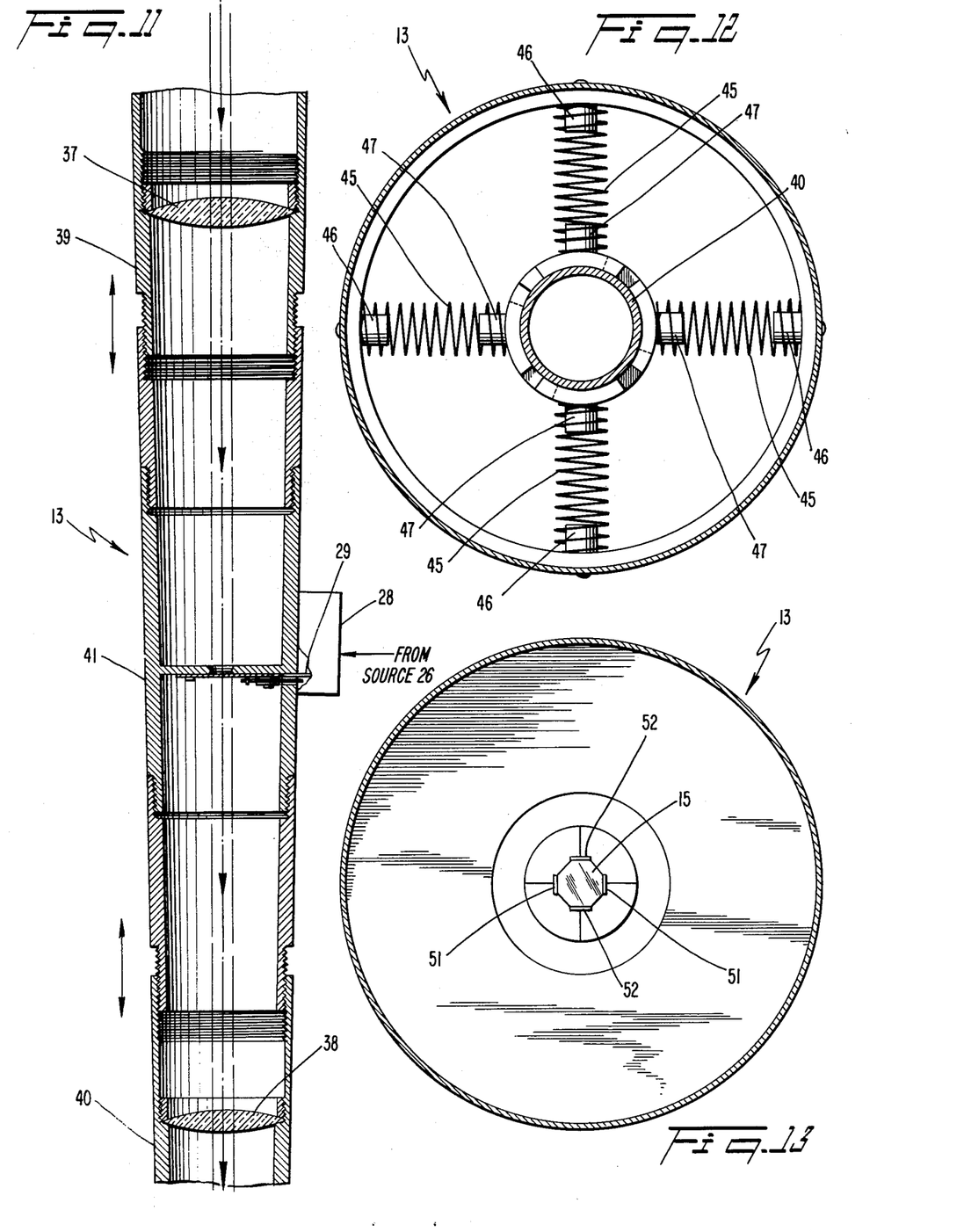
FIG. 11 is a sectional view of the collimator illustrated in FIG. 3.
FIG. 12 is a sectional view of the collimator taken through the lines 12—12, FIG. 3.
FIG. 13 is a top view of an electrically responsive optical deflector positioned immediately in front of the entrance optical aperture of the cannula, and taken along the lines 13—13, FIG. 4.
Figure 14:
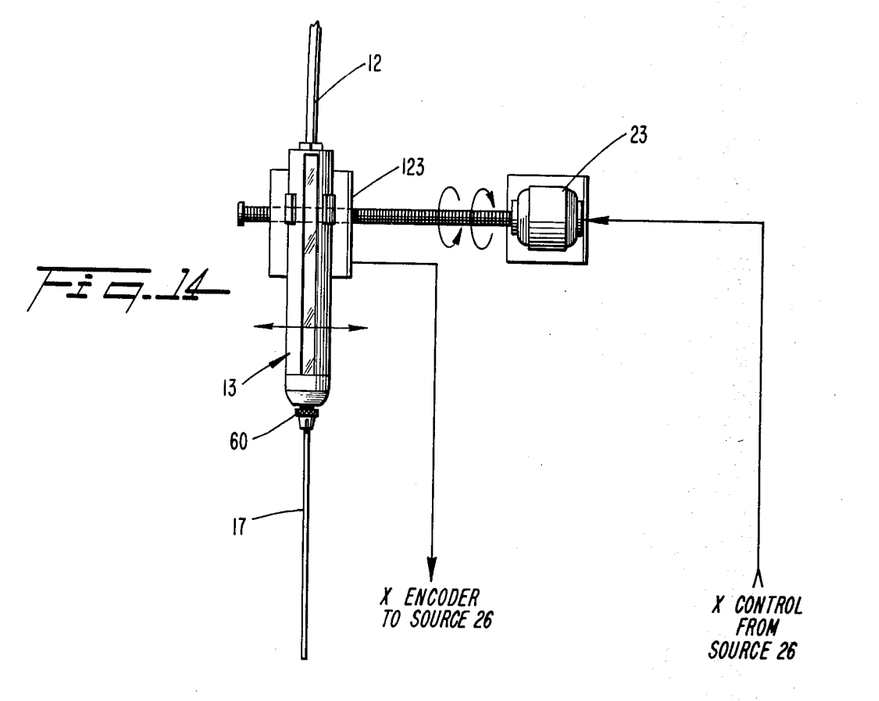
FIG. 14 is a circuit diagram of a servo control system for positioning the collimator and cannula along one axis of the cannula.
Figure 15:
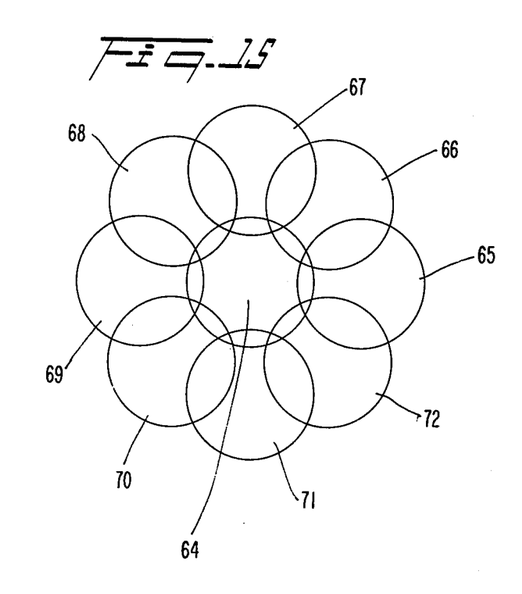
FIG. 15 is a view indicating the manner in which tissue is excised at a single position of the cannula in response to deflection of the laser beam.

The beam exiting wave guide 12 has a circular cross section, typically with a diameter of 0.8 inches. The beam is reduced in diameter by collimator 13 so that the beam exiting the collimator has a diameter anywhere in a wide range of 0.006 to 0.020 inches. To provide this relatively wide range of beam diameters and to maintain confocality of the beam, collimator 13 includes lenses 37 and 38 that are respectively fixedly mounted in tubular sections 39 and 40, between which is disposed tubular section 41. Opposite ends of section 41 are threaded into sections 39 and 40 to enable lenses 37 and 38 to be translated relative to each other to vary the focusing of the collimator and diameter of the beam exiting the collimator. Lenses 9, 37 and 38 are manufactured of a suitable material so they are transparent to the radiant energy derived from laser 11 and opaque to other wavelengths, thereby to enhance the transmittivity of the collimator to the wavelength of laser source 11.

Normally, closed shutter 29, fixedly mounted in the central portion of section 41, blocks the passage of the beam through collimator 13. The aperture of shutter 29 can be controlled to vary the diameter and depth field of the beam propagating through the collimator. For a beam in the $TEM_{02}$ mode having a diameter of 0.8 inches that enters collimator 13, the aperture of shutter 29 is related to the f number, focal depth, focal spot size and front working distance of collimator 13 as follows:

TABLE I

| Aperture Size | Focal Length | Front Working Distance From Exit Aperture of Lens | Focal Depth | Focal Spot Size | Volume of Excised Tissue For Beam Depth of 2mm Into Tissue |
|---|---|---|---|---|---|
| .10" | 5.0" | 4.9" | .33" | 0.020" | 1 cm$^3$ |
| .33" | 1.5" | 1.3" | .030" | 0.002" | 1 mm$^3$ |

The focal depth in Table I is the distance at which the spot size is not more than 40% greater than at focus.

In one preferred embodiment, shutter 29 includes five blades and a built-in ten-leaf iris diaphragm. The speed of shutter 29 can be set anywhere in the range from 4 seconds to 125th of a second, depending upon the depth of tissue desired to be excised each time a laser pulse is coupled through cannula 17 to treated organism 19. Shutter 29 is opened in synchronism with step-wise deflection of the laser beam by crystal 15. Changing shutter 29, by selective removal of section 41, and changing lenses 37 and 38, by selective removal of sections 39 and 40, enables the wide range of beam diameters to be attained.

As illustrated in FIG. 12, sections 39 and 40 are respectively held in situ relative to cylindrical wall 42 of collimator 13 by radially directed spring assemblies 43 and 44. Spring assemblies 43 and 44 are substantially identical, each including four radially directed springs 45, FIG. 12, held in place between radially directed studs 46 on the interior wall of cylinder 42 and studs 47 that project outwardly from section 40.

Light beam deflector 15 is fixedly positioned at the exit aperture of collimator 13. Light beam deflector 15 is either an electro-optical switch or an acousto-optical switch that causes angular displacement of the beam incident thereon. The selection of an electro-optical or acousto-optical switch is determined by the wavelength of the laser radiation emitted by source 11. In either case, the crystal includes two sets of mutual orthogonal electrodes 51 and 52, FIG. 13, which are respectively responsive to X and Y beam deflection fed through two pairs of leads in cable 27 from control source 26. With zero voltage applied to electrode pairs 51 and 52, the beam incident on crystal 15 is not deflected and propagates along an axis coincident with the bore sight axis of optically transparent bore 16 within cannula 17. In response to nonzero deflection voltages being applied to electrode pairs 51 and 52, the beam propagating through bore 16 is gyrated relative to the cannula bore sight axis.

Figure 16:
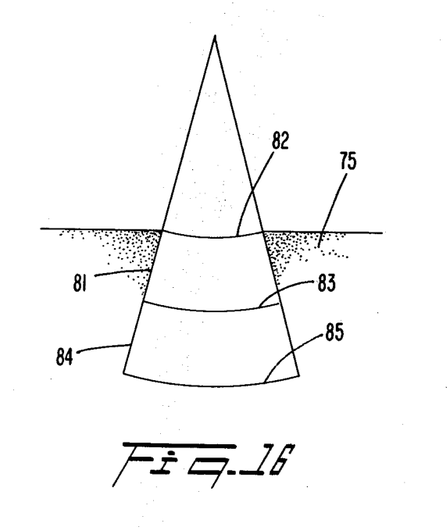
FIG. 16 is a side sectional view, at right angles to the surface of the pathological tissue, indicating the manner in which tissue is excised from two different layers at a single cannula position in response to laser beam deflection.

Preferably, the voltages are applied in a step-wise manner to electrode pairs 51 and 52 in synchronism with opening of shutter 29. The step-wise voltages are applied to electrode pairs 51 and 52 so that, in a preferred embodiment, the beam is deflected to eight positions about the bore sight axis of cannula 17, as illustrated in FIG. 16. At each of the eight positions, a relatively small amount of energy from the beam intercepts the wall of bore 16, but most of the beam energy passes through the bore and impinges with a substantially circular cross section on the region in organ 19 that is aligned with the deflected beam axis. The beam deflection and diameter are such that initially a first region, having a center coincident with the bore sight axis of bore 16, is excised from the pathological tissue in the organ. In response to each subsequent deflection of the beam, additional regions having centers substantially coincident with the deflected propagation axis are excised from the pathological tissue of the irradiated organ. Each of the additional regions has a peripheral portion overlapping, e.g. by approximately 20%, a peripheral portion of the first region to excise frusto-conical segments from the organism.

In one preferred embodiment, deflector 15 is an electro-acoustic transducer formed of a germanium crystal or alloy, so it is compatible with $CO_2$ laser radiation with a wavelength of 10.6 microns. In a second embodiment, wherein a semiconductor neodymium laser is utilized, crystal 15 is a gallium arsenide crystal.

Germanium has a relatively high index of refraction, approximately 4.0, low optical absorption and a high optical figure of merit. By maximizing the figure of merit, the amount of power required to drive the germanium crystal is minimized. In one particular embodiment, single crystal germanium is employed because it has one or more facets having high figures of merit. Because one or more facets of germanium have high figures of merit, the crystal can be oriented to expose different crystal facets to the incident laser beam in response to an acoustic signal induced by the germanium in response to the electric signal coupled to electrode pairs 51 and 52. The optical strain in crystal 15, resulting from the acoustic signal (typically ultrasonic pulses having a carrier centered at 25 MHZ) changes the refractive index of the germanium, resulting in beam deflection and polarization changes. The beam deflection angle depends on the acoustic frequencies coupled to the crystal. In one preferred embodiment, the acoustic frequencies are such that the beam is deflected to eight different angles, each having the same radius relative to the bore sight axis of bore 16 and equi-angularly displaced from each other by 45°. The beam is deflected by crystal 15 through only a relatively small angle, such as ±0.1° relative to the bore sight axis of cannula 17. The combined parameters of focusing lens 9 and the deflection angle of the beam by crystal 15 and the inner and outer diameters of cannula 17 are such that the beam remains confocal as it propagates through bore 16, whereby Gaussian distribution of the beam exiting the bore is maintained and the angle of the beam exiting the cannula is accurately controlled. Because bore 16 includes a metallic reflecting surface 71 that introduces a secondary reflection on the beam propagating through cannula 17, the ±0.1° deflection introduced by deflector 15 is translated into a ±0.6° deflection of the beam exiting cannula 17.

In the electro-optical embodiment, deflecting crystal 15 is fabricated of two abutting crystals having mutually orthogonal polarization axes. Mutually orthogonal electrodes are secured to edges of the two crystals to achieve the same type of deflection as is achieved with the acousto-optical deflector.

Invasive cannula 17 is fabricated of pyrolytic graphite having a crystal orientation enabling it to be nonmetallic along some axes and metallic along other axes and to have very low thermal conductivity in the radial direction, at right angles to the cannula longitudinal axis. Cannula 17 is removably secured to the exit end of collimator 13 by a chuck 58 having jaws 59 that grasp the exterior of the cannula under the control of nut 60. Different cannulas are selectively inserted into chuck 58. If the patient is very large, cannula 17 has a relatively long length, on the order of 6 inches, in contrast to an average person wherein cannula 17 need have a length only on the order of approximately 4 inches.

Cannula 17 may also be changed because it is desired to utilize cannulas having differing diameters for bore 16. If it is necessary to form a relatively large, low resolution hole in the tissue of the patient, the diameter of bore 16 would be approximately 5 millimeters, but for other applications the bore diameter is as small as 25 microns. The wall of a large diameter bore has a coating 53 formed by electroplating walls a stable, high optical reflectivity and high thermal conductivity coating 53 of metal, preferably gold, on the wall of bore 16. Coating 53 is covered with a thin dielectric, preferably germanium, film 72 as illustrated in FIG. 5. If bore 16 has a very small diameter, less than 500 microns, where electroplating metal film 53 and dielectric film 72 might be difficult, the bore is filled with a dielectric core of a material having a high index of refraction and which will maintain confocality; isotropic polycrystalline germanium, having a refractive index of approximately 3, is a preferred material for carbon dioxide lasers having a wavelength of 10.6 microns.

The beam propagating through bore 16 preferably has a diameter of between 50% and 100% of the bore diameter. If, however, very high resolution is required, the diameter of bore 16 is less than the diameter of the beam incident on its entrance aperture. The resulting loss in beam power is necessary in certain instances where resolution is more important than total energy incident on the pathological tissue. Because of the confocal nature of the focussing system, the beam exiting bore 16 has a substantially circular cross section even when deflected by crystal 15.

In one embodiment that was actually constructed, cannula 17 had inner and outer diameters of approximately 5 and 10 millimeters, respectively. Cannula 17 was fabricated in this instance by depositing carbon on alumina tubing and/or graphite pins tubing at high temperatures. After cooling, the pins were separated, leaving a hollow pyrolytic carbon tubing with an inner alumina bore wall. The inner wall was then electroplated with gold film 53 that is then covered with dielectric film 72, to form an air bore 16. If the transparent portion 16 of cannula 17 is a solid dielectric, the gold and dielectric coating steps are omitted and the dielectric is packed as a powder into a central hollow bore of the cannula. Because cannula 17 has a pyrolytic carbon crystalline structure with a very low thermal conductivity in the radial direction of the cannula, there is very little heat transferred from the interior wall of bore 16 to the exterior wall of the cannula. Thereby, tissue in contact with the exterior wall of cannula 17 is not excessively heated and burned, despite the high temperature (approximately 1700° to 1800° C.) of the medium (either air or the dielectric) which is propagating the laser beam. The use of pyrolytic carbon for cannula 17 has the additional advantages of biocompatibility and non-thrombogenic properties because it is chemically inert with human and other animal tissue.

As indicated in connection with FIGS. 1, and 6-10 the present invention is particularly adaptable to be used in connection with certain surgical problems of the heart. For heart surgery, a prior art monitoring device, such as an EKG and/or a set of electrodes mounted on the heart, is utilized to determine that area 61 of the heart has pathological tissue to be excised. While area 61, in the heart wall close to the bottom of the left ventricle is illustrated, it is to be understood that other portions of the heart could have pathological tissue to be removed. The approximate location of area 61 is initially determined from the QRS complex of the electrocardiogram and is then exactly determined from an array of electrodes placed directly on the heart in the vicinity of the left ventricle, as known to those skilled in the art. Based upon the information derived from the EKG, incision 18 is made in the chest cavity in the proximate location of the pathological heart tissue. After the heart has been visually analyzed through the incision and the location of area 61 exactly determined with the array, the array is removed. The array gives the exact region within the heart containing the pathological tissue. The region is programmed as command signals for motors 23-25 into control source 26. The cannula having the largest inner diameter is then inserted into chuck 58. To remove blood and tissue to be excised, known suction devices are inserted into the cavity in proximity with the portion of the heart containing the pathological tissue. Cannula 17 is positioned above incision 18 by driving assembly 21 with X and Y motors 23 and 24. Cannula 17 is then driven through incision 18 in response to control source 26 supplying a Z signal to motor 25 so that cannula 17 invades the body cavity. Cannula 17 is driven by motors 23 and 24 in response to X and Y control signals from source 26 to a position above pathological tissue 61 outside of pericardium sac 62, FIG. 7. Bore sight axis 16 of cannula 17 is now substantially at right angles to the exterior surface including pathological tissue 61. Then laser 11 is activated and shutter 29 is opened so that a coherent optical, pulsed beams 63 is supplied to circular area 64 of sac 62 in alignment with bore sight axis 16 of cannula 17. Shutter 29 is then closed and a programmed deflecting voltage is applied from source 26 to electrodes 51 of light beam deflector 15. With the deflecting voltage applied to electrodes 51, shutter 29 is opened again, causing the laser beam derived from cannula 17 to impinge on a second, circular region 65, displaced along the X axis from, but overlapping with the periphery of region 64, on sac 62. Shutter 29 is then closed, after which equal deflecting voltages are applied to electrodes 51 and 52 of crystal 15. Shutter 29 is then opened again, whereby third circular region 66, having a center displaced 45° from the X and Y axes, is irradiated on sac 62. The periphery of region 66 is in abutting relationship with the periphery regions 64 and 65. This procedure is continued from regions 67-72 so eight different regions surround central region 64 to form an excised tissue region on sac 62, without moving cannula 17.

As each of regions 64-72 is formed, shutter 29 is opened for a sufficient length of time to enable sac 62 to be completely pierced by the laser beam propagating from cannula 17. Usually, the hole pierced in sac 62 by the beam propagated from cannula 17, at a single position of the cannula, is not a sufficient radius to enable the cannula to be inserted through the hole. Hence, after a first frusto-conical hole has been pierced in sac 62 at one position of cannula 17, assembly 21 is incrementally moved to a second position in response to programming signals from source 26 supplying new signal values to X and Y to motors 23 and 24. Motors 23 and 24 drive assembly 21 to a new position in a plane parallel to the exterior surface of pathological tissue 61. Motors 23 and 24 are activated until X and Y position transducers 123 and 124 indicate that the X and Y positions of cannula 17 are the same as the command signals applied by source 26 to motors 23 and 24. The second position for assembly 21 is such that cannula 17 will produce a second frusto-conical aperture in pericardial sac 62 at a position adjacent and abutting the first frusto-conical aperture. Usually, it is necessary to position cannula 17 at four different, mutually orthogonal locations to provide an aperture 76 in sac 62 with sufficient area to enable the cannula to be inserted through the sac, and in proximity to wall 75 in which pathological tissue 61 is situated. The four positions of cannula 17 enable four abutting frusto-conical holes, that together form a hole resembling a square, to be pierced in sac 62.

Figures 6, 7, 8:
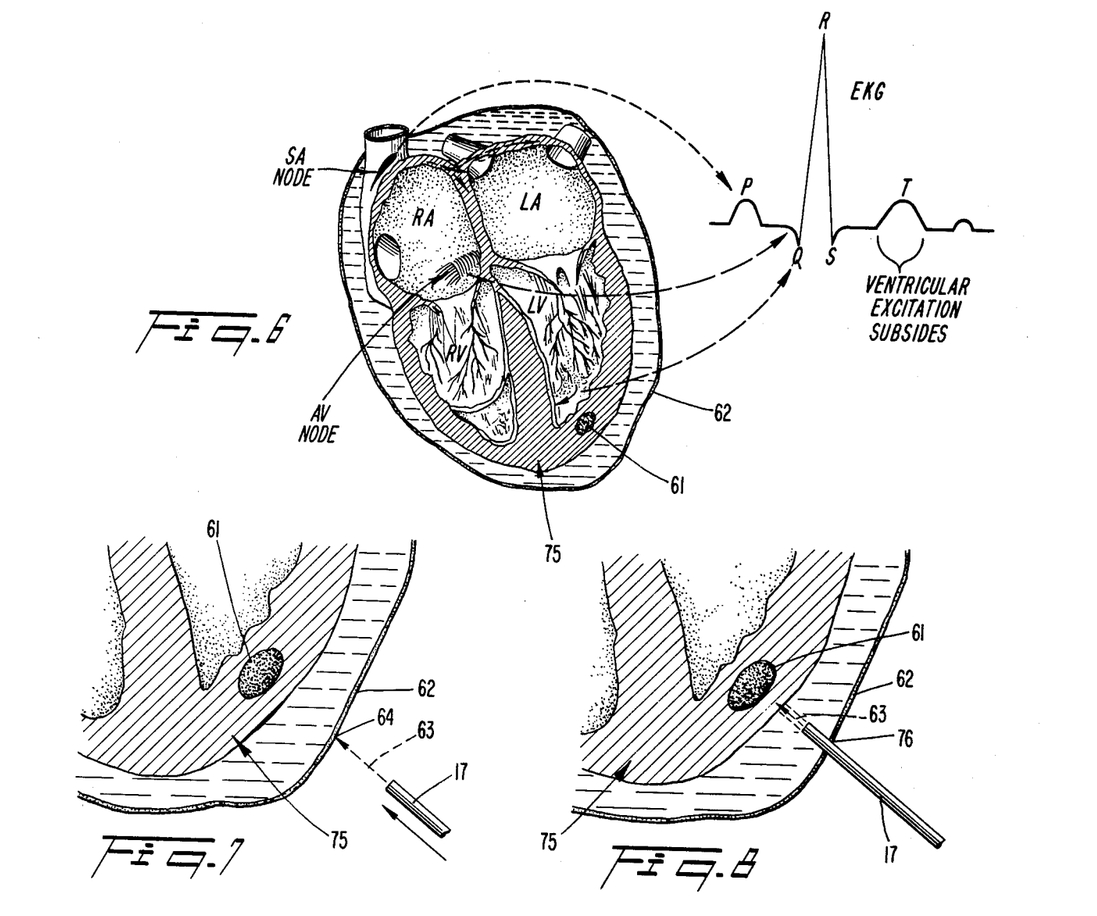
FIG. 6 is a view of the heart containing pathological tissue in the interior of the heart wall.
FIGS. 7-10 are illustrious of steps involved in excising pathological tissue from the heart in accordance with the method of the invention.
Figure 9:
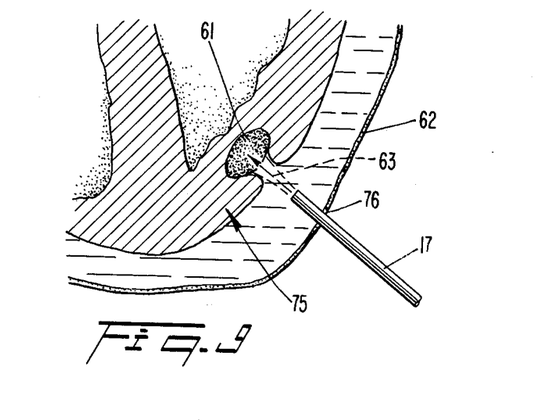

After the four holes have been formed in sac 62, cannula 17 is repositioned in the center of the four holes in response to X and Y command signals from source 26 that activates motors 23 and 24. Source 26 then activates motor 25 so assembly 21 is advanced through the hole pierced in sac 62 into proximity with wall 75. As illustrated in FIG. 8, Z axis motor 25 drives assembly 21 invasively through hole 76 in sac 62 until the Z axis position of assembly 21, as determined by position encoder 125, is coincident with the Z axis command signal derived from control source 26. Alternatively, cannula 17 is withdrawn from the body cavity and a second cannula, having a smaller diameter bore than the cannula utilized to pierce sac 62, replaces the original cannula. Frequently, it is desirable to utilize a cannula having a smaller diameter bore for subsequent operations because of the smaller beam diameter which enables greater resolution to be obtained. In such instances, it may not be necessary to reposition cannula 17 to form an aperture of sufficient area in sac 62 to enable a high resolution, small outer diameter cannula to be inserted through the sac. Withdrawal of cannula 17 from the body cavity need not be accompanied by an X or Y movement of assembly 21, in which case the cannula remains aligned with the hole pierced in sac 62.

After cannula 17 has been replaced, or if the same cannula remains on chuck 58, assembly 21 is advanced through the pierced hole in sac 62, into proximity with the surface of heart wall 75 containing pathological tissue 61, as indicated by FIG. 8. Cannula 17 is moved through hole 76 pierced in sac 62 by activating Z axis motor 25 while maintaining the X and Y positions of the cannula stationary. With cannula 17 at rest in proximity to surface 75, laser 11 is again activated and shutter 29 is opened with no voltage applied to electrodes 51 and 52 of deflecting crystal 15. Thereby, an on-axis hole is pierced in the surface of wall 75. Because tissue 61 is in the interior of heart wall 75, shutter 29 remains open for a relatively long interval, such as a second. After the on-axis hole has been bored in wall 75 and a segment of pathological tissue 61 has been removed, shutter 29 is closed. Then, deflecting voltages are sequentially applied to electrodes 51 and 52 of light deflector 15 and shutter 29 is sequentially opened, whereby eight bores are formed in wall 75 and into a portion of pathological tissue 61 in abutting relation with the periphery of the on-axis bore, as described supra in connection with FIG. 16.

A layer excised from heart wall 75 has a generally frusto-conical volume 81, as illustrated in FIG. 16. Volume 81 has generally concave bases 82 and 83 respectively at the surface of wall 75 and within the wall. Base 83 has a greater area than base 82 because excising beam 63 is deflected by crystal 15, to eight positions surrounding the on-axis beam position.

After layer 81 of pathological tissue 61 has been removed, the EKG trace is inspected to determine if the abnormality in the wave form has been rectified. Alternatively, cardiac mapping electrodes are again placed on the heart and signals from the electrodes are analyzed to determine if the functional abnormality has been rectified. If the abnormality has not been rectified and it is due to additional pathological tissue at the site within the field of view of the beam propagating from cannula 17, a frusto-conical second deeper layer 84 of pathological tissue is removed by again illuminating the pathological tissue with a series of nine pulses. Layer 84 has an area, in the X-Y plane, greater than the area layer 81 because of deflection of the beam propagating from cannula 17. Each of layers 81 and 84 has a concave floor, with floor 85 of layer 84 being greater than the floor 83 of layer 81 because floor 85 is farther from exit aperture of cannula 17 than is floor 83. While pathological tissue 61 is exercised from layers 81 and 84, assembly 21 is maintained rigid.

The diameter of the excised tissue can range from 25 microns to approximately 12 millimeters for one position of cannula 17. The 25 micron diameter hole is achieved by utilizing a cannula having a transparent solid bore with a diameter of 25 microns, without beam deflection. The 12 millimeter diameter bore is formed with a cannula having an air bore having a diameter of approximately 5 millimeters and by utilizing a deflection sequence involving 9 different pulses propagated through cannula 17 to the pathological tissue.

In many instances, however, it is necessary to excise 1 to 2 cubic centimeters of pathological tissue. In such an instance, a relatively large diameter aperture is bored in pericardial sac 62 and programmed control voltages are supplied to motors 23 and 24 to move cannula 17 in a plane parallel to the surface of wall 75 to cover a significant area. To remove such a large mass of pathological tissue, cannula 17 is driven to a plurality of X-Y positions, and at each position a deflection sequence is performed with the cannula maintained stationary. After the cannula has moved to each of the programmed positions, the monitoring apparatus is examined and a decision is made as to whether additional pathological tissue must be removed. If so, the assembly 21 is again driven by motors 23 and 24 over the same path as that additional tissue is excised, to a greater depth, from the same area. Alternatively, it may be decided that only a certain portion of the same path need be covered again, in which case the control voltages supplied by source 26 to motors 23 and 24 are reprogrammed.

Figure 10:
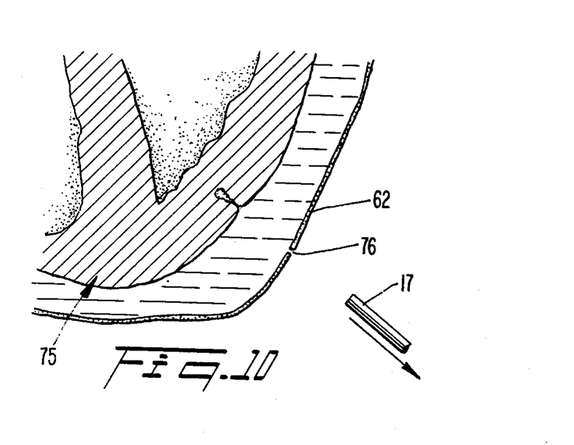

After all of the pathological tissue has been excised, the wound heals relatively quickly because of the precision with which the destructive energy is delivered to the pathological tissue. In addition, the diameter of the aperture on the surface of wall 75 is less than the diameter of the aperture in the pathological tissue, below the surface (unless a very small diameter hole is bored) so that the surface tissue binds together before the internal tissue, as illustrated in FIG. 10, which also indicates the cannula 17 has been withdrawn from sac 62. Of course, if a very small diameter hole (25 microns) is formed, it heals very quickly. After the excised tissue has been removed, assembly 21 is driven by motor 25 in the Z axis direction to withdraw cannula 17 from the body cavity. Thereafter, the function of the heart is monitored repeatedly by EKG to ensure that the pathological tissue has been excised from the heart and normal function has been restored. The operation is concluded in the usual manner.

While there have been described and illustrated several specific embodiments of the invention, it will be clear that variations in the details of the embodiments specifically illustrated and described may be made without departing from the true spirit and scope of the invention as defined in the appended claims. For example, the apparatus can be utilized to excise other pathological tissue, particularly in the brain.

I claim:

1. An instrument for excising pathological tissue from a living animal organism comprising means for emitting a beam of coherent optical radiation, collimating means responsive to the beam for reducing the beam cross sectional area, a pyrolytic graphite cannula having an optically transparent interior responsive to the reduced diameter beam, said cannula coupling the reduced diameter beam onto the tissue so the tissue is irradiated by the beam, said reduced diameter beam having sufficient energy to vaporize the irradiated tissue, the graphite of the cannula having a crystalline structure orieinted whereby heating of the cannula interior by radiation from the beam is not substantially transferred by conduction to the exterior of the cannula.

2. The instrument of claim 1 wherein the transparent cannula interior is an air filled bore extending longitudinally through the cannula, said bore having a reflecting wall.

3. The instrument of claim 1 wherein the transparent cannula interior comprises a dielectric filled bore extending longitudinally through the cannula.

4. The instrument of claim 1, or 2 or 3 wherein the collimator includes means for variably reducing the beam cross section.

5. A method of excising pathological tissue from a heart without mechanically cutting the pericardial sac surrounding the heart comprising inserting a cannula through an opening in the body cavity and into proximity with a region of the sac above a site from which the tissue is to be removed, then propagating a beam of coherent optical radiation through the cannula to burn a hole in the sac, the hole having sufficient area to enable the cannula to be inserted through it, then inserting the cannula through the hole in the sac and positioning the cannula so its longitudinal axis is aligned with the site, then maintaining the cannula stationary and irradiating the site with a beam of coherent optical radiation propagated through the cannula to remove the tissue.

6. The method of claim 5 wherein the irradiating beam is gyrated about the longitudinal axis while the cannula is maintained stationary to forma frusto-conical removed region in the tissue, the frusto-conical region having a base adjacent the tissue surface smaller than a base removed from the tissue surface.

7. The method of claim 6 wherein the irradiating beam is gyrated by being stepwise directed to adjacent, overlapping subregions in the tissue so the beam is stationary as it irradiates each of the subregions and is not propagated to the tissue while it is gyrated between the subregions.

8. The method of claim 5, or 6, or 7 further including monitoring characteristics of the heart after the tissue has been removed, then repeating the irradiation step while maintaining the cannula stationary to remove additional tissue from the irradiated site, and then repeating the monitoring step.

9. The method of claim 8 further including monitoring characteristics of the heart after the tissue has been removed, then moving the cannula into proximity with a different region of the sac above another site which the monitoring indicated to contain pathological lesions, then repeating the propagating, inserting, irradiating and monitoring steps for tissue at another site.

10. The method of claim 5, or 6, or 7 comprising the step of reducing the cross sectional area of the irradiating beam relative to the area of the beam that burns a hole in the pericardial sac.

11. A method of excising pathological tissue from an organism comprising positioning a cannula through an opening in the organism into proximity with the tissue to be excised so the longitudinal axis of the cannula is aligned with a site of the tissue, then maintaining the cannula stationary while irradiating the site with a beam of coherent optical radiation propagated longitudinally through the cannula to remove the tissue, peripheral portions of the site being irradiated by gyrating the beam about the cannula axis, a central portion of the site being irradiated by propagating the beam along the cannula axis and not gyrating it about the cannula axis.

12. The method of claim 11 wherein the gyration of the beam is controlled by coupling the beam to an electronically controlled optical crystal deflector having a fixed position, and applying deflecting voltages to the crystal deflector to provide the gyration.

13. A method of excising pathological tissue from an organism comprising positioning a cannula through an opening in the organism into proximity with the tissue to be excised so the longitudinal axis of the cannula is aligned with a site of the tissue, then maintaining the cannula stationary while irradiating the site with a beam of coherent optical radiation propagated longitudinally through the cannula to remove the tissue, the site being irradiated by gyrating the beam about the cannula axis, the irradiating beam being gyrated by being stepwise directed to adjacent, overlapping subregions in the tissue so the beam is stationary as it irradiates each of the subregions and is not propagated to the tissue while it is gyrated between the subregions.

14. The method of claim 11 or 13 further including monitoring characteristics of the organism after the tissue has been removed, then repeating the irradiation step while maintaining the cannula stationary to remove additional tissue from the irradiated site and then repeating the monitoring step.

15. An instrument for excising pathological tissue from an organism comprising a laser for deriving a beam of coherent optical energy, an optical waveguide responsive to the beam, a collimator responsive to the beam exiting the waveguide for reducing the beam cross sectional area, and a graphite cannula responsive to the beam exiting the collimator, said cannula having a longitudinal optically transparent bore sight axis for coupling the reduced cross section area beam to the tissue, the graphite of the cannula having a crystalline structure oriented whereby heating of the cannula interior by radiation from the beam is not substantially transferred by conduction to the exterior of the cannula.

16. The instrument of claim 15 further including means for mounting the cannula so the cannula bore sight axis is coincident with an axis extending at substantially right angles through an exterior surface of the tissue, and motor means for moving the cannula so its bore sight axis moves in a plane at right angles to a plane on an exterior surface containing the tissue.

17. The instrument of claim 15 or claim 16 further including means for translating the cannula along its bore sight axis.

18. The instrument of claim 17 further including an electrically responsive optical deflector fixedly positioned with respect to the cannula for coupling the reduced cross sectional beam exiting the collimator to the cannula bore sight axis and for gyrating the reduced cross sectional area beam about the bore sight axis.

19. The instrument of claim 15 or 16 further including an electrically responsive optical deflector fixedly positioned with respect to the cannula for coupling the reduced cross sectional beam exiting the collimator to the cannula bore sight axis and for gyrating the reduced cross sectional area beam about the bore sight axis.

20. A method of excising pathological tissue from an organism comprising (a) directing a bore sight axis of a beam source of radiation capable of excising the tissue at the tissue so the bore sight axis is substantially at right angles to a first region of the tissue, (b) pulsing the beam on while it is directed at the first region, the beam irradiating the tissue having a predetermined cross sectional area to excise tissue in the first region, the first region having a center coincident with the bore sight axis and an extent away from the center equal to the area of irradiation, (c) deflecting the beam propagation axis by a predetermined axis off the bore sight axis while the beam is off, so the beam is directed at a second region of the tissue, the second region having a center substantially coincident with the deflected propagation axis and a peripheral portion overlapping a peripheral portion of the first region, (d) pulsing the beam on while it is directed at the second region to excise tissue in the second region, repeating steps (c) and (d) for a sufficient number of positions about the bore sight axis to excise tissue from all regions of the organism abutting the periphery of the first region, whereby an excision having a substantially frusto-conical cross section at right angles to the surface of the organism is provided in the organism, said frusto-conical cross section having a smaller base on the surface of the organism than within the organism.

* * * * *